United States Patent [19]

Simon et al.

[11] Patent Number: 4,508,704

[45] Date of Patent: Apr. 2, 1985

[54] RADIOACTIVE METALS COMPLEXED WITH PHOSPHONATE DERIVATIVES OF BICYCLOHEPTANE BIS(ALKYLAMINES)

[75] Inventors: Jaime Simon, Angleton; David A. Wilson, Richwood, both of Tex.; Wynn A. Volkert, Columbia, Mo.

[73] Assignee: The Dow Chemical Company, Midland, Mich.

[21] Appl. No.: 584,070

[22] Filed: Feb. 27, 1984

[51] Int. Cl.$^3$ .................. A61K 49/00; A61K 43/00
[52] U.S. Cl. .................. 424/14; 260/429 J; 260/429.2; 260/429.7; 260/502 E; 562/499; 424/9
[58] Field of Search .............. 424/1.1, 9; 562/499; 260/429 J, 429.2, 429.7, 502.5 E

[56] References Cited

U.S. PATENT DOCUMENTS

| | | | |
|---|---|---|---|
| 3,851,044 | 11/1974 | Adler et al. | 423/249 |
| 3,852,414 | 12/1974 | Adler et al. | 424/1 |
| 3,931,396 | 1/1976 | Bardy et al. | 424/1 |
| 3,983,227 | 9/1976 | Tole et al. | 424/1 |
| 3,989,730 | 11/1976 | Subramanian et al. | 260/429.7 |
| 4,016,249 | 4/1977 | Adler et al. | 424/1 |
| 4,032,625 | 6/1977 | Subramanian et al. | 424/1 |
| 4,075,314 | 2/1978 | Wolfangel et al. | 424/1 |
| 4,082,840 | 4/1978 | Adler et al. | 424/1 |
| 4,387,087 | 6/1983 | Deutsch et al. | 424/1.1 |

OTHER PUBLICATIONS

Radiology, vol. 99, pp. 192–196, 1971.
Radiology, 136: 209–211, Jul. 1980.
Radiology, 136: pp. 747–751, Sep. 1980.
J. Nuc. Med. 21: pp. 767–770, (1980).
J. Nuc. Med. 21, pp. 961–966, (1980).

*Primary Examiner*—Christine M. Nucker
*Attorney, Agent, or Firm*—A. C. Ancona

[57] ABSTRACT

New stable complexing agents for Tc-99m which are phosphonate derivatives of bicycloheptane bis(alkylamines) have been found which are useful in imaging the skeletal system in animals. The complexes readily clear through the kidneys with large amounts being taken up in the bone. The ratio of uptake in bone to that in soft tissue is high.

20 Claims, No Drawings

RADIOACTIVE METALS COMPLEXED WITH PHOSPHONATE DERIVATIVES OF BICYCLOHEPTANE BIS(ALKYLAMINES)

BACKGROUND OF THE INVENTION

The first radionuclide to be widely used for bone scanning was Sr-85. Strontium-85 is rapidly accumulated by bone after intravenous administration and images of the skeletal system are possible. However, Sr-85 has a long physical half life (65 days) and a long biological half life (~800 days) which limits the levels which can be administered. Also, the high energy of the gamma photon emitted (514 kev) is difficult to collimate.

Fluorine-18 has also been used to image the skeletal system. It is a positron emitter with a half life of 1.85 hr. Although F-18 has good physical properties for imaging, it has some serious drawbacks. Fluorine-18 is cyclotron produced and, therefore, expensive. Also its distribution is limited due to its short half life.

Many organ scanning agents, including those for the skeletal system, have now been replaced with complexes of Technetium-99m. This nuclide has ideal physical properties ($T_\frac{1}{2}$=6 hr., gamma photon of 141 kev) for imaging. In addition, it is readily available because of the Mo-99/Tc-99m generators. Thus, the majority of imaging is now done using Tc-99m.

Technetium-99m is obtained from generators in the +7 oxidation state as the pertechnetate ion ($TcO_4^-$). In order to form a complex, Tc must be in a lower oxidation state, i.e. +3, +4 or +5. Although other reducing agents can be used, $Sn^{2+}$ has been employed most often. Thus Tc-99m complexes can be formed by reduction of $TcO_4^-$ using $Sn^{2+}$ in the presence of a complexing agent. This is usually done in an aqueous saline solution that is suitable for intravenous injection.

Commercial complexing agents are sold as "radiopharmaceutical kits". A "kit" consists of an evacuated vial containing the complexing agent, a reducing agent, and possibly a buffer and stabilizers. To prepare the Tc-99m complexes, a few milliliters of sodium pertechnetate solution in saline is injected into the vial. An adequate amount of the resultant solution is used for imaging.

Subramanian et al (Radiology, Vol. 99, pp. 192–196, 1971) reported the use of a complex of Tc-99m and an inorganic polyphosphate for skeletal imaging. Several others have reported inorganic polyphosphates as useful for this purpose (see U.S. pat. Nos. 3,852,414; 4,016,249; and 4,082,840). The use of pyrophosphate (PYP) for bone imaging has also been taught (U.S. Pat. Nos. 3,851,044; 3,931,396; and 4,075,314). The Tc-phosphates had fair success but have been replaced by Tc-phosphonates.

Complexes of Tc-99m with phosphonic acids show higher bone uptake with faster blood clearance than Tc-99m/phosphate complexes. Phosphonic acids which are considered the best bone scanning agents when complexed with Tc-99m include hydroxyethanediphosphonate (EHDP), methylenediphosphonate (MDP) and hydroxymethylenediphosphonate (see U.S. Pat. Nos. 3,983,227; 3,989,730; 4,032,625 and also J. Nucl. Med. 21, pg. 767; Radiology 136, pg. 209; J. Nucl. Med. 21, pg. 961; Radiology 136, pg. 747).

Another application for radioactive chelates is as therapeutic agents. It may be possible to treat bone tumors with a particle emitting radionuclide if it can be concentrated in the area of the tumor. For example, if a beta-emitting agent that had a high uptake in bone tumor and relatively low uptake in normal bone was found, it could prove to be an effective therapeutic agent.

Several nuclides may be of therapeutic utility. For example Re-186 has a half life of 90.6 hr. and beta-radiation of 1.076 and 0.939 MeV. Also, since the chemistry of Re is very similar to that of Tc, it is probable that the biolocalization of Re-complexes would be similar to that of Tc-complexes. (see Weinenger, J., Ketring, A. R., et al., J. Nucl. Med., 24, p. 23, 1983). There are other nuclides, especially of the lanthanide group of metals, that may also be therapeutically useful.

SUMMARY OF THE INVENTION

New stable complexing agents for Tc-99m which are phosphonate derivatives of bicycloheptane bis(alkylamines) have been found which are useful in imaging the skeletal system in animals. The complexes readily and efficiently clear through the kidneys with large amounts being taken up in the bone. The ratio of uptake in bone to that in soft tissue is high.

DETAILED DESCRIPTION OF THE INVENTION

This invention concerns the use of novel complexes for imaging the skeletal system and for possible treatment of skeletal metastasis. The complexing agents were found to form stable Tc-99m complexes when $Sn^{2+}$ was added to a saline solution containing the complexing agent. The complex clears readily through the kidneys with a large amount being taken up by the skeletal system and very little was left in the blood and soft tissue.

Therefore, since the ratio of uptake in bone to that of surrounding soft tissue is high, the images were sharp and clear. Ratios of activity in bone/soft tissue and bone/blood compare favorably to commercial Tc-bone radiopharmaceuticals.

The complexing agents useful in this invention, are derivatives of bicyclo(2,2,1)heptane. The complexing agents are prepared from bis(alkylamines) derived from the bicycloheptane. These compounds and their method of preparation are disclosed in our concurrently filed and copending application entitled "New Metal Ion Control Compounds Based on Norbornane", (Docket No. C-32,709.

The structure of the complexing agents has the following formula

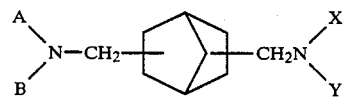

wherein substituents A, B, X and Y each are independently selected from radicals consisting of hydrogen, hydroxyalkyl (wherein the alkyl group contains 2-6 carbon atoms), methylenephosphonic, methylene-, ethylene- and propylenesulfonic, carboxylic acid radicals (having 2-4 carbon atoms) and the alkali or alkaline earth metal, ammonia and amine salts of any of the phosphonic, sulfonic or carboxylic acid derivatives. At least one of the substituents must be other than a hydrogen.

The following examples illustrate the method of preparation and the utilization of the subject compounds.

EXAMPLE 1

Distilled water (10 g) and $H_3PO_3$ (9.9 g) were weighed into a 50-ml round-bottom flask equipped with a water-cooled condenser, a thermometer, a stirring bar, and an addition funnel. Concentrated HCl (11.8 g) was then added and 3.9 g of (1)2,4(5)bis[aminomethyl]-bicyclo(2,2,1)heptane was slowly added while stirring. The solution was heated at reflux for approximately one hour and a 37% aqueous formaldehyde solution (8.51 g) was added over a period of 2.5 hours. The solution was heated for an additional 3 hours at reflux.

One hundred μl of the above solution was placed in a vial and one ml of 0.9% saline (aq.) was added. The pH of the solution was adjusted to 3.5 using dilute NaOH and HCl and 0.1 ml of a freshly eluted $TcO_4^-$ solution was added. This was followed by the addition of 100 μl of a saturated stannous tartrate solution. Elution of paper chromatography strips with saline and acetone showed less than 5% of the activity as $TcO_4^-$ or reduced uncomplexed Tc.

The above Tc-complex (50 μl, ~1 mCi) was injected in the tail vein of rats. Scintillation scans of the anesthetized rats were taken at several intervals post injection. The bone scans were of high quality implying the use of this as a tool for human patients.

EXAMPLE 2

The Tc-ccomplex prepared in Example 1 (50 μl, ~1 mCi) was injected in the tail vein of mice. The mice were killed at different times post injection, the organs and tissues removed, and the radiation measured with a NaI counter. The activity was found primarily in the bone, and bladder with no other organs showing a high affinity for the complex. At 120 minutes post-injection, the bone, muscle, and liver had, respectively, 5.1, <0.01, 0.24% dose/g of the activity.

EXAMPLE 3

The Tc-complex of Example 1 (50 μl, ~1 mCi) was injected into the tail vein of a series of rats. The animals were killed after 2 hours and the radiation from several tissues was quantitated using a NaI scintillation counter. The table below shows the results compared to Tc-MDP*, commercial Tc-bone agent, evaluated in an identical manner.
*MDP=methylenediphosphonate

| Organ | Percent Dose/Organ of Several Tissues in Rats | |
|---|---|---|
| | Complex of Example 1 | Commercial Agent (Tc-MDP) |
| Skeleton | 41.7 | 39.4 |
| Blood | 0.23 | 0.27 |
| Urine | 63.1 | 50.9 |
| Ratios | | |
| Bone/blood | 181 | 146 |
| Bone/muscle | 384 | 150 |

EXAMPLE 4

The complex of Example 1 was injected in the ear vein of a series of rabbits. The rabbits were killed 3 hours after injection. The radiation of several tissues was quantified by counting using a NaI scintillation counter. The table below shows the results compared to those of a commercial Tc-bone agent, MDP.

| Organ | % Dose × 1% Body Wt. / Gram in Several Tissues in Rabbits | |
|---|---|---|
| | Complex of Example 1 | Commercial Agent, Tc-MDP |
| Femur | 5.3 | 5.7 |
| Liver | 0.07 | 0.11 |
| Muscle | 0.03 | 0.05 |
| Blood | 0.10 | 0.13 |
| Ratios | | |
| Femur/blood | 53 | 44 |
| Femur/muscle | 177 | 114 |

Scintillation scans of the above rabbits 2 hours after injections with the complex of Example 1 compared favorably with those using Tc-MDP commercial kits.

We claim:

1. A bone seeking complex of a radioactive nuclide and a compound having the structural formula

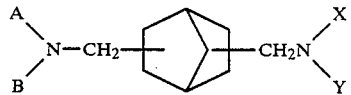

wherein substituents A, B, X and Y each are independently selected from radicals consisting of hydrogen, hydroxyalkyl (wherein the alkyl group contains 2–6 carbon atoms), methylenephosphonic; methylene-, ethylene- and propylenesulfonic; alkylcarboxylic acid radicals (having 2–4 carbon atoms) and the alkali, alkaline earth metal, ammonium and amine salts of any of the phosphonic, sulfonic or carboxylic acid derivatives, and wherein at least one of the substituents is other than hydrogen.

2. The complex of claim 1 wherein A, B, X and Y are each methylenephosphonic acid radicals or salts thereof.

3. The complex of claim 1 wherein the radioactive nuclide is Technetium-99m.

4. The complex of claim 2 wherein the radioactive nuclide is Technetium-99m.

5. A composition comprising the complex of claim 3 and a reducing agent in a saline solution.

6. A composition comprising the complex of claim 4 and a reducing agent in a saline solution.

7. The composition of claim 5 wherein the reducing agent is $Sn^{2+}$.

8. The composition of claim 6 wherein the reducing agent is $Sn^{2+}$.

9. The composition of claim 1 wherein the radioactive nuclide is a particle emitter.

10. The composition of claim 2 wherein the radioactive nuclide is a particle emitter.

11. The composition of claim 9 wherein the radionuclide is Re-186.

12. The composition of claim 10 wherein the radionuclide is Re-186.

13. A composition comprising the complex of claim 11 and a reducing agent in a saline solution.

14. A composition comprising the complex of claim 12 and a reducing agent in a saline solution.

15. The composition of claim 13 wherein $Sn^{2+}$ is the reducing agent.

16. The composition of claim 14 wherein $Sn^{2+}$ is the reducing agent.

17. The composition of claim 9 wherein the radionuclide is one of the lanthanide series of the periodic table.

18. The composition of claim 10 wherein the radionuclide is one of the lanthanide series of the periodic table.

19. In a process in which the skeletal system is imaged with a complex of a radionuclide the improvement which comprises employing as the complexing agent a compound having the formula

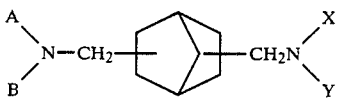

wherein substituents A, B, X and Y each are independently selcted from radicals consisting of hydrogen, hydroxyalkyl (wherein the alkyl group contains 2-6 carbon atoms), methylenephosphonic; methylene-, ethylene- and propylenesulfonic; alkylcarboxylic acid radicals (having 2-4 carbon atoms) and the alkali, alkaline earth metal, ammonium and amine salts of any of the phosphonic, sulfonic or carboxylic acid derivatives, and wherein at least one of the substituents is other than hydrogen.

20. The process of claim 19 wherein A, B, X and Y are each methylenephosphonic acid or a salt thereof.

* * * * *

UNITED STATES PATENT AND TRADEMARK OFFICE
CERTIFICATE OF CORRECTION

PATENT NO. : 4,508,704

DATED : April 2, 1985

INVENTOR(S) : Jaime Simon; David A. Wilson; Wynn A. Volkert

It is certified that error appears in the above-identified patent and that said Letters Patent is hereby corrected as shown below:

Col. 2, line 49, delete [(Docket No. C-32,709] and insert --(now U.S. 4,500,469)--.

Col. 3, line 33, change "Tc-ccomplex" to --Tc-complex--.

Col. 6, line 9, change "selcted" to --selected--.

Signed and Sealed this

Third Day of September 1985

[SEAL]

*Attest:*

DONALD J. QUIGG

*Attesting Officer*    Acting Commissioner of Patents and Trademarks - Designate